(12) United States Patent
Chen et al.

(10) Patent No.: US 11,578,058 B2
(45) Date of Patent: Feb. 14, 2023

(54) HETEROCYCLIC COMPOUNDS FOR INHIBITING TYK2 ACTIVITIES

(71) Applicant: Beijing InnoCare Pharma Tech Co., Ltd., Beijing (CN)

(72) Inventors: Xiangyang Chen, Beijing (CN); Yucheng Pang, Beijing (CN)

(73) Assignee: Beijing Innocare Pharma Tech Co., Beijing (CN)

(*) Notice: Subject to any disclaimer, the term of this patent is extended or adjusted under 35 U.S.C. 154(b) by 0 days.

(21) Appl. No.: 17/736,866

(22) Filed: May 4, 2022

(65) Prior Publication Data

US 2022/0259184 A1 Aug. 18, 2022

Related U.S. Application Data

(63) Continuation of application No. PCT/CN2021/079752, filed on Mar. 9, 2021.

(60) Provisional application No. 62/988,317, filed on Mar. 11, 2020.

(51) Int. Cl.
*C07D 403/12* (2006.01)

(52) U.S. Cl.
CPC .................... *C07D 403/12* (2013.01)

(58) Field of Classification Search
CPC .................................................. C07D 403/12
See application file for complete search history.

(56) References Cited

FOREIGN PATENT DOCUMENTS

| | | |
|---|---|---|
| CN | 104884454 A | 9/2015 |
| CN | 106660960 A | 5/2017 |
| CN | 111484480 A | 8/2020 |
| WO | 2014/074661 A1 | 5/2014 |
| WO | 2015/069310 A1 | 5/2015 |
| WO | 2020/086616 A1 | 4/2020 |
| WO | 2020/156311 A1 | 8/2020 |

OTHER PUBLICATIONS

International Search Report for International Application No. PCT/CN2021/079752, dated Jun. 10, 2021 (7 pages).
Wrobleski, S.T. Highly Selective Inhibition of Tyrosine Kinase 2 (TYK2) for the Treatment of Autoimmune Diseases: Discovery of the Allosteric Inhibitor BMS-986165. J. Med. Chem., Jul. 18, 2019 (23 pages).

*Primary Examiner* — Brian E McDowell
(74) *Attorney, Agent, or Firm* — Perkins Coie LLP; Viola Kung

(57) ABSTRACT

The present invention is directed to Compounds 1-8, and their pharmaceutically acceptable salts or prodrugs thereof. Compounds 1-8 are selective binders to TYK2's JH2 and they exhibit significant inhibitory effects on the physiological function of TYK2 and they have excellent in vivo pharmacokinetic properties. Compounds 1-5 and 7 have several deuterium substitutions on methyl to improve pharmacokinetic (PK) properties.

8 Claims, 2 Drawing Sheets

HETEROCYCLIC COMPOUNDS FOR INHIBITING TYK2 ACTIVITIES

This application is a continuation of PCT/CN2021/079752, filed Mar. 9, 2021; which claims the benefit of U.S. Provisional Application No. 62/988,317, filed Mar. 11, 2020. The contents of the above-identified applications are incorporated herein by reference in their entirety.

FIELD OF THE INVENTION

The present invention relates to heterocyclic compounds useful in the modulation of TYK2 to cause signal transduction inhibition. The compounds provide improved pharmacokinetic properties in animals.

BACKGROUND OF THE INVENTION

Tyrosine kinase 2 (TYK2) is a non-receptor tyrosine protein kinase belonging to the Janus kinase (JAK) family and has been shown to be critical in regulating the signal transduction cascade downstream of receptors for IL-12, IL-23 and type I interferons.

The tandem kinase domains are the hallmark of JAKs. JH1 is a canonical protein tyrosine kinase domain, whereas JH2 is classified as a pseudokinase domain. The structure of JAK family is shown in FIG. 1.

Recent biochemical and structural data suggest that the pseudokinase domain of TYK2 has low levels of catalytic activity and negatively regulates the activity of the kinase domain.

When the cytokine receptors bind the cytokines, the phosphorylation of TYK2 and its other family members JAK1 and/or JAK2 that are bound to the intracellular regions is triggered, resulting in activation of signal transduction and transcriptional activation factors (STATs) by dimerization. The dimerized STATs then migrate inside the nucleus and regulate the expression and transcription of related genes to complete the transduction of signals from the cell membrane to the nucleus. Therefore, JAKs transduce cytokine-mediated signals through the JAK-STAT pathway and play an important role in many cellular functions, cytokine-dependent regulation of cell proliferation, differentiation, apoptosis, immune response, etc. TYK2-deficient mice are resistant to experimental models of colitis, psoriasis and multiple sclerosis, demonstrating the importance of TYK2-mediated signaling in autoimmunity and related disorders.

In humans, individuals expressing an inactive variant of TYK2 are protected from multiple sclerosis and possibly other autoimmune disorders. Genome-wide association studies have shown that other variants of TYK2 are associated with autoimmune disorders such as Crohn's disease, psoriasis, systemic lupus erythematosus, and rheumatoid arthritis, further demonstrating the importance of TYK2 in autoimmunity.

TYK2 knockout mice have normal red blood cell counts and they are able to survive. Lack of TYK2 expression is manifested in the weakened signaling of various pro-inflammatory cytokines and the severe imbalance of T helper cell differentiation. Evidence from genetic-related studies supports TYK2 as a shared susceptible autoimmune disease gene. TYK2-regulated pathways have been confirmed by antibody therapy for treating diseases. For example, ustekinumab targeting IL-12/IL-23 for treating psoriasis, and anifrolumab targeting type I interferon receptor for treating systemic lupus erythematosus (SLE) have demonstrated significant efficacies in clinical trials.

TYK2 is associated with some cancers by the correlation between abnormal survival of acute lymphocytic leukemia (T-ALL) cells and the activation of TYK2. As an oncogene of T-ALL, 88% of T-ALL cell lines and 63% of patient-derived T-ALL cells were dependent on TYK2 via gene knockout experiments (Sanda et. al, Cancer Disc. 2013, 3, 564-77). TYK2 selective inhibitor NDI-031301 induced apoptosis to inhibit the growth of human T-ALL cell lines and showed good safety and efficacy in a mouse model with KOPT-K1 T-ALL tumor cells (Akahane et. al, British J. Haematol. 2017, 177, 271-82), which demonstrates the prospect of selective inhibitors of TYK2 for treating T-ALL. Therefore, TYK2 is one of the hot targets for treating inflammatory diseases, autoimmune diseases and cancer (Alicea-Velazquez et. al, Curr. Drug Targets 2011, 12, 546-55).

TYK2 and other members of the JAK family structurally have a kinase domain JH1 (JAK Homology 1) and an adjacent pseudokinase domain JH2 (JAK Homology 2). JH2 can bind ATP, but it does not have a catalytic function and instead it negatively regulates the kinase activity of JH1 (Staerk et. al, J. Biol. Chem. 2015, 280, 41893-99). Due to high sequence similarity of the kinase domain JH1 among the JAK family (JAK1, JAK2, JAK3, and TYK2), it is challenging to develop a selective inhibitor towards TYK2's JH1 without inhibiting the JH1 of JAK1, JAK2, or JAK3. Most JAK inhibitors that bind to the kinase domain of JAKs, including tofacitinib, ruxolitinib, baricitinib, upadacitinib, etc., are not very selective among the JAK family members and exhibit dose-dependent side effects clinically such as anemia. The development of highly selective TYK2 inhibitors remains attractive among pharmaceutical companies. Based on the structural differences between the ATP binding pockets in TYK2's JH1 and JH2, Bristol-Myers Squibb Company has developed a highly selective JH2 binder BMS-986165, which only inhibits the physiological functions mediated by TYK2 without binding to the kinase domains (JH1) of JAKs. BMS-986165 is now in the Phase III clinical trials for autoimmune diseases (Wrobleski et. al, J. Med. Chem. 2019, 62, 8973-95).

The structure of BMS-986165 is shown below (WO2014/074661):

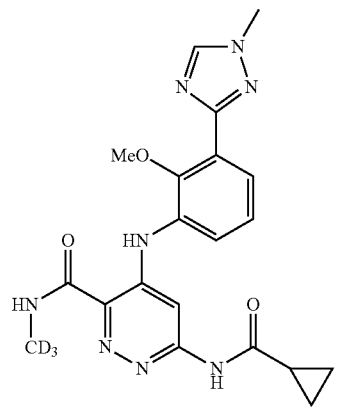 [SMILES: [2H]C([2H])([2H])NC(=O)c1nnc(NC(=O)C2CC2)cc1Nc1cccc(-c2ncn(C)n2)c1OC]

There remains a need to develop new compounds that selectively binds to the pseudokinase domain (JH2) of TYK2, with minimal binding toward kinase domains of the JAK families, in particular JAK2.

DETAILED DESCRIPTION OF THE INVENTION

Figure 1:
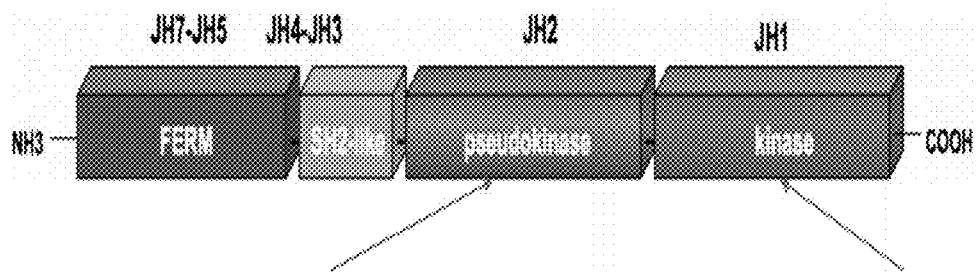
FIG. 1 shows the common secondary structure of JAK family (JAK1, JAK2, JAK3, and TYK2).

The inventors have discovered selective TYK2 inhibitors not targeting on the catalytically active site of TYK2, but targeting on the TYK2 pseudokinase domain (JH2). The present invention is directed to Compounds 1-8, and their pharmaceutically acceptable salts or prodrugs thereof. Compounds 1-8 are selective binders to JH2 of TYK2. By binding to the pseudokinase domain (JH2), Compounds 1-8 inhibit the kinase catalytic activity of TYK2, inhibit protein phosphorylation, and exhibit significant inhibitory effects on the physiological function of TYK2. Compounds 1-8 either bind weakly or do not bind to the kinase domain (JH1) of TYK2. Compounds 1-8 selectively inhibits the kinase activity of TYK2 by binding to JH2 and have low inhibitory activity toward the kinase activity of other JAK family members. The selectivity of Compounds 1-8 for inhibiting TYK2 over other JAK family members (JAK1, JAK2, and JAK3) minimizes side effects such as anemia. Compounds 1-8 are shown to have excellent in vivo pharmacokinetic properties in animals.

| Compound No. | Structure and Name |
|---|---|
| 1 | 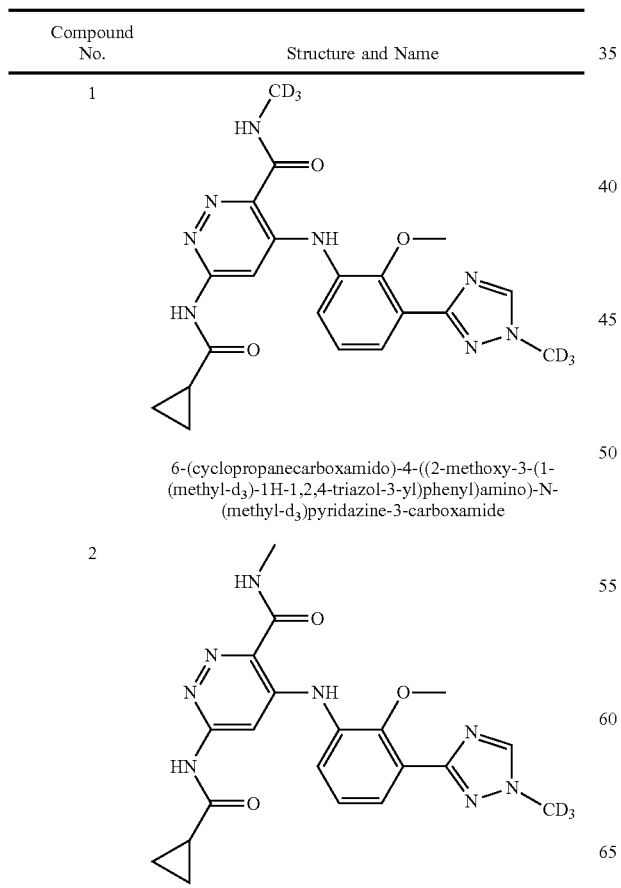 6-(cyclopropanecarboxamido)-4-((2-methoxy-3-(1-(methyl-$d_3$)-1H-1,2,4-triazol-3-yl)phenyl)amino)-N-(methyl-$d_3$)pyridazine-3-carboxamide |
| 2 | 6-(cyclopropanecarboxamido)-4-((2-methoxy-3-(1-(methyl-$d_3$)-1H-1,2,4-triazol-3-yl)phenyl)amino)-N-methylpyridazine-3-carboxamide |
| 3 | 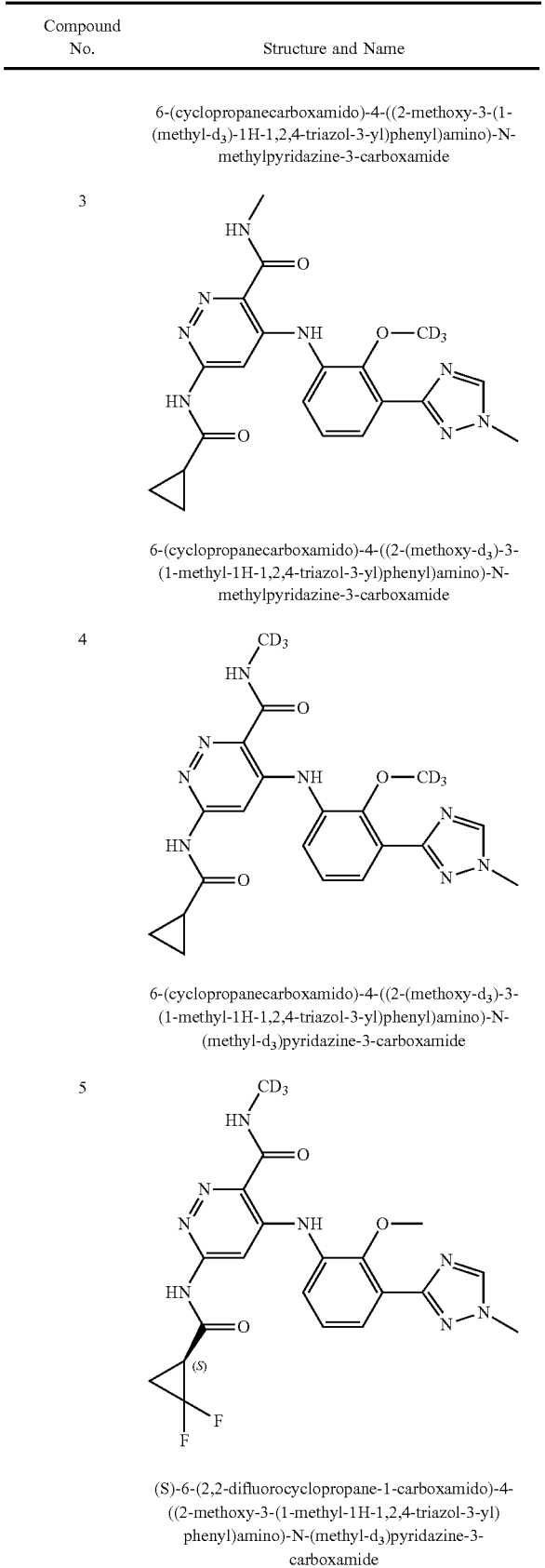 6-(cyclopropanecarboxamido)-4-((2-(methoxy-$d_3$)-3-(1-methyl-1H-1,2,4-triazol-3-yl)phenyl)amino)-N-methylpyridazine-3-carboxamide |
| 4 | 6-(cyclopropanecarboxamido)-4-((2-(methoxy-$d_3$)-3-(1-methyl-1H-1,2,4-triazol-3-yl)phenyl)amino)-N-(methyl-$d_3$)pyridazine-3-carboxamide |
| 5 | (S)-6-(2,2-difluorocyclopropane-1-carboxamido)-4-((2-methoxy-3-(1-methyl-1H-1,2,4-triazol-3-yl)phenyl)amino)-N-(methyl-$d_3$)pyridazine-3-carboxamide |

| Compound No. | Structure and Name |
|---|---|
| 6 | 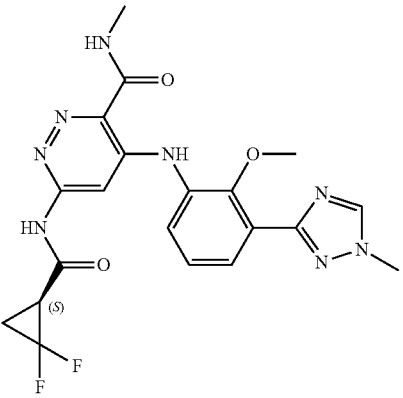<br>(S)-6-(2,2-difluorocyclopropane-1-carboxamido)-4-((2-methoxy-3-(1-methyl-1H-1,2,4-triazol-3-yl)phenyl)amino)-N-methylpyridazine-3-carboxamide |
| 7 | 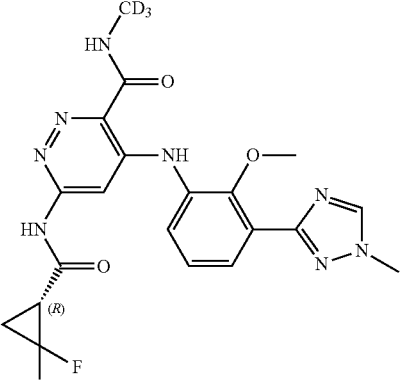<br>(R)-6-(2,2-difluorocyclopropane-1-carboxamido)-4-((2-methoxy-3-(1-methyl-1H-1,2,4-triazol-3-yl)phenyl)amino)-N-(methyl-d$_3$)pyridazine-3-carboxamide |
| 8 | 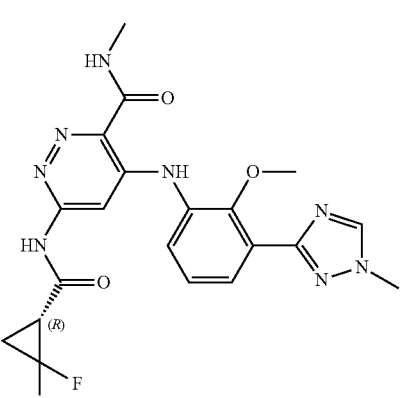<br>(R)-6-(2,2-difluorocyclopropane-1-carboxamido)-4-((2-methoxy-3-(1-methyl-1H-1,2,4-triazol-3-yl)phenyl)amino)-N-methylpyridazine-3-carboxamide |

"Pharmaceutically acceptable salts", as used herein, are salts that retain the desired biological activity of the parent compound and do not impart undesired toxicological effects. Pharmaceutically acceptable salt forms include various crystalline polymorphs as well as the amorphous form of the different salts. The pharmaceutically acceptable salts of the present basic heterocyclic compounds can be formed with inorganic acids or organic acids.

"Prodrug", as used herein, refers to a compound which, upon administration to a subject, undergoes chemical conversion by metabolic or chemical processes to yield the compound of Compounds 1-8, and/or a salt thereof. Any compound that will be converted in vivo to provide the bioactive agent of Compound 1-8 is a prodrug within the scope of the invention. Various forms of prodrugs are well known in the art.

Compound 1 has tri-deuterated methyl on the triazole ring and tri-deuterated methyl amide.

Compound 2 has tri-deuterated methyl on the triazole ring.

Compound 3 has tri-deuterated methoxy on the benzene ring.

Compound 4 has tri-deuterated methoxy on the benzene ring and tri-deuterated methyl amide.

Compound 5 has (S)-6-(2,2-difluorocyclopropane-1-carboxamido) and tri-deuterated methyl amide.

Compound 6 has (S)-6-(2,2-difluorocyclopropane-1-carboxamido) without any deuterium substitution.

Compound 7 has (R)-6-(2,2-difluorocyclopropane-1-carboxamido) and tri-deuterated methyl amide.

Compound 8 has (R)-6-(2,2-difluorocyclopropane-1-carboxamido) without any deuterium substitution.

Compounds 1-5 and 7 have several deuterium substitutions on methyl to improve pharmacokinetic (PK) properties. Compounds 5-8 have difluoro on cyclopropane. The compounds of the present invention have low binding activities toward JAKs' kinase domains and have high inhibitory activities against TYK2's cellular functions such as inhibiting the secretion of y-interferon and IL-23. The compounds of the present invention provide good bioavailability when administered orally. The compounds of the present invention are safe to use and are effective in treating inflammatory bowel disease (IBD), as demonstrated in an anti-CD40 colitis (IBD) model in mice, which showed no significant body weight loss after treatment with Compounds 2, 3, and 5.

Pharmaceutical Compositions

The present invention provides pharmaceutical compositions comprising one or more pharmaceutically acceptable carriers and an active compound of Compounds 1-8, or a pharmaceutically acceptable salt thereof. The active compound or its pharmaceutically acceptable salt in the pharmaceutical compositions in general is in an amount of about 0.01-20%, or 0.05-20%, or 0.1-20%, or 0.2-15%, or 0.5-10%, or 1-5% (w/w) for a topical formulation; about 0.1-5% for an injectable formulation, 0.1-5% for a patch formulation, about 1-90% for a tablet formulation, and 1-100% for a capsule formulation.

In one embodiment, the active compound is incorporated into any acceptable carrier, including creams, gels, lotions or other types of suspensions that can stabilize the active compound and deliver it to the affected area by topical applications. In another embodiment, the pharmaceutical composition can be in a dosage form such as tablets, capsules, granules, fine granules, powders, syrups, suppositories, injectable solutions, patches, or the like. The above pharmaceutical composition can be prepared by conventional methods.

Pharmaceutically acceptable carriers, which are inactive ingredients, can be selected by those skilled in the art using conventional criteria. Pharmaceutically acceptable carriers include, but are not limited to, non-aqueous based solutions, suspensions, emulsions, microemulsions, micellar solutions, gels, and ointments. The pharmaceutically acceptable carriers may also contain ingredients that include, but are not limited to, saline and aqueous electrolyte solutions; ionic and nonionic osmotic agents such as sodium chloride, potassium chloride, glycerol, and dextrose; pH adjusters and buffers such as salts of hydroxide, phosphate, citrate, acetate, borate; and trolamine; antioxidants such as salts, acids and/or bases of bisulfite, sulfite, metabisulfite, thiosulfite, ascorbic acid, acetyl cysteine, cysteine, glutathione, butylated hydroxyanisole, butylated hydroxytoluene, tocopherols, and ascorbyl palmitate; surfactants such as lecithin, phospholipids, including but not limited to phosphatidylcholine, phosphatidylethanolamine and phosphatidyl inositiol; poloxamers and poloxamines, polysorbates such as polysorbate 80, polysorbate 60, and polysorbate 20, polyethers such as polyethylene glycols and polypropylene glycols; polyvinyls such as polyvinyl alcohol and povidone; cellulose derivatives such as methylcellulose, hydroxypropyl cellulose, hydroxyethyl cellulose, carboxymethyl cellulose and hydroxypropyl methylcellulose and their salts; petroleum derivatives such as mineral oil and white petrolatum; fats such as lanolin, peanut oil, palm oil, soybean oil; mono-, di-, and triglycerides; polymers of acrylic acid such as carboxypolymethylene gel, and hydrophobically modified cross-linked acrylate copolymer; polysaccharides such as dextrans and glycosaminoglycans such as sodium hyaluronate. Such pharmaceutically acceptable carriers may be preserved against bacterial contamination using well-known preservatives, these include, but are not limited to, benzalkonium chloride, ethylenediaminetetraacetic acid and its salts, benzethonium chloride, chlorhexidine, chlorobutanol, methylparaben, thimerosal, and phenylethyl alcohol, or may be formulated as a non-preserved formulation for either single or multiple use.

For example, a tablet formulation or a capsule formulation of the active compound may contain other excipients that have no bioactivity and no reaction with the active compound. Excipients of a tablet or a capsule may include fillers, binders, lubricants and glidants, disintegrators, wetting agents, and release rate modifiers. Binders promote the adhesion of particles of the formulation and are important for a tablet formulation. Examples of excipients of a tablet or a capsule include, but not limited to, carboxymethylcellulose, cellulose, ethylcellulose, hydroxypropylmethylcellulose, methylcellulose, karaya gum, starch, tragacanth gum, gelatin, magnesium stearate, titanium dioxide, poly(acrylic acid), and polyvinylpyrrolidone. For example, a tablet formulation may contain inactive ingredients such as colloidal silicon dioxide, crospovidone, hypromellose, magnesium stearate, microcrystalline cellulose, polyethylene glycol, sodium starch glycolate, and/or titanium dioxide. A capsule formulation may contain inactive ingredients such as gelatin, magnesium stearate, and/or titanium dioxide.

For example, a patch formulation of the active compound may comprise some inactive ingredients such as 1,3-butylene glycol, dihydroxyaluminum aminoacetate, disodium edetate, D-sorbitol, gelatin, kaolin, methylparaben, polysorbate 80, povidone, propylene glycol, propylparaben, sodium carboxymethylcellulose, sodium polyacrylate, tartaric acid, titanium dioxide, and purified water. A patch formulation may also contain skin permeability enhancer such as lactate esters (e.g., lauryl lactate) or diethylene glycol monoethyl ether.

Topical formulations including the active compound can be in a form of gel, cream, lotion, liquid, emulsion, ointment, spray, solution, and suspension. The inactive ingredients in the topical formulations for example include, but not limited to, diethylene glycol monoethyl ether (emollient/permeation enhancer), DMSO (solubility enhancer), silicone elastomer (rheology/texture modifier), caprylic/capric triglyceride, (emollient), octisalate, (emollient/UV filter), silicone fluid (emollient/diluent), squalene (emollient), sunflower oil (emollient), and silicone dioxide (thickening agent).

Method of Use

The inventor has demonstrated that the present compounds specifically bind to TYK2's pseudokinase domain (JH2) and significantly inhibit the physiological function of TYK2 in NK92 cells. The compounds also show excellent pharmacokinetic properties in rats.

The present invention is directed to a method for preventing or treating TYK2-mediated diseases, including, but not limited to, autoimmune diseases, inflammatory diseases (including intestinal inflammation and bowel inflammation), cancers, skin diseases, diabetes, eye diseases, neurodegenerative diseases, allergic reactions, asthma, other obstructive airway diseases and transplant rejection, etc. The method is particularly useful for treating inflammatory bowel disease, psoriasis, and systemic lupus erythematosus (SLE). The method comprises administering to a patient in need thereof an effective amount of a compound of the present invention, or a prodrug thereof, a pharmaceutically acceptable salt thereof. "An effective amount," as used herein, is the amount effective to treat a disease by ameliorating the pathological condition or reducing the symptoms of the disease.

The pharmaceutical composition of the present invention can be applied by local administration and systemic administration. Local administration includes topical administration. Systemic administration includes oral (including buccal or sublingual), parenteral (such as intravenous, intramuscular, subcutaneous or rectal), and other systemic routes of administration. In systemic administration, the active compound first reaches plasma and then distributes into target tissues. Topical administration and oral administration are preferred routes of administration for the present invention.

Dosing of the composition can vary based on the extent of the injury and each patient's individual response. For systemic administration, plasma concentrations of the active compound delivered can vary; but are generally $1 \times 10^{-10}$-$1 \times 10^{-4}$ moles/liter, and preferably $1 \times 10^{-8}$-$1 \times 10^{-5}$ moles/liter.

In one embodiment, the composition is applied topically onto the affected area and rubbed into it. The composition is topically applied at least 1 or 2 times a day, or 3 to 4 times per day, depending on the medical issue and the disease pathology being chronic or acute. In general, the topical composition comprises about 0.01-20%, or 0.05-20%, or 0.1-20%, or 0.2-15%, 0.5-10, or 1-5% (w/w) of the active compound. The active compound passes through skin and is delivered to the site of discomfort.

In one embodiment, the pharmaceutical composition is administrated orally to the subject. The dosage for oral administration is generally at least 0.1 mg/kg/day and less than 1000 mg/kg/day. For example, the dosage for oral administration is 0.5 mg to 1 g, preferably 1 mg to 700 mg, or 5 mg to 300 mg of a compound per day.

Those of skill in the art will recognize that a wide variety of delivery mechanisms are also suitable for the present invention.

The present invention is useful in treating a mammal subject, such as humans, horses, and dogs. The present invention is particularly useful in treating humans.

The following examples further illustrate the present invention. These examples are intended merely to be illustrative of the present invention and are not to be construed as being limiting.

EXAMPLES

Examples 1-8 illustrate the synthesis of the present compounds. The product in each step of the reaction is obtained by separation techniques known in the art including, but not limited to, extraction, filtration, distillation, crystallization, and chromatographic separation. The starting materials and chemical reagents required for the synthesis can be conventionally synthesized according to the literature (available searching from SciFinder) or purchased.

The structure of a compound is determined by nuclear magnetic resonance (NMR) or mass spectrometry (MS). The NMR was measured using a Bruker ASCEND-400 NMR spectrometer. The solvents were deuterated dimethylsulfoxide (DMSO-$d_6$), deuterated chloroform ($CDCl_3$), or deuterated methanol ($CD_3OD$). The internal standard was tetramethylsilane (TMS). The chemical shift is provided in unit of $10^{-6}$ (ppm).

MS was measured using an Agilent SQD (ESI) mass spectrometer (manufacturer: Agilent, model: 6120).

HPLC was measured using an Agilent 1260 DAD high pressure liquid chromatography (Poroshell120 EC-C18, 50×3.0 mm, 2.7 μm column) or Waters Arc high pressure liquid chromatography (Sunfire C18, 150×4.6 mm, 5 μm column).

Thin-layer chromatography (TLC) was run using Qingdao Ocean GF254 silica gel plate. The specification of TLC for reaction monitoring and production separation/purification is 0.15~0.2 mm and 0.4~0.5 mm thick, respectively.

Column chromatography was run generally using Qingdao Ocean silica gel 200-(300 mesh) as the carrier.

The known starting materials used in the present invention may be synthesized according to the methods known in the art, or may be purchased from ABCR GmbH & Co. KG, Acros Organics, Sigma-Aldrich Chemical Company, Accela ChemBio Inc., Beijing Ouhe chemicals, and other companies.

In the examples below, unless otherwise specified, the reactions were all carried out under an argon atmosphere or a nitrogen atmosphere.

The hydrogenation reaction was usually run in a reactor that is evacuated, charged with hydrogen and repeatedly operated three times.

The microwave reaction was run using a CEM Discover-SP microwave reactor.

In the examples below, unless otherwise specified, the reaction temperature was room temperature from 20° C. to 30° C.

The reaction progress was monitored by an Agilent LCMS instrument (1260/6120). It might also be monitored by TLC. The solvent system for TLC was A: a dichloromethane and methanol system; B: a petroleum ether and ethyl acetate system; C: a system shown in the examples. The volume ratio of the solvents was adjusted according to the polarity of the compound.

The eluent system for column chromatography and TLC used in the process of compound purification included A: a dichloromethane and methanol system; B: a petroleum ether and ethyl acetate system; C: a system shown in the examples. The volume ratio of the solvents was adjusted according to the polarity of the compound, and a small amount of triethylamine and an acidic or basic reagent could be added for adjustment.

The purification of compound could also be carried out using a Waters' mass spectrometry-oriented automated preparation system (prep-HPLC with a mass detector of SQD2). Depending on the polarity of the compound, an appropriate acetonitrile/water (containing 0.1% trifluoroacetic acid or formic acid) or acetonitrile/water (containing 0.05% ammonium hydroxide) elution profile was used to wash a reversed phase high pressure column (XBridge-C18, 19×150 mm, 5 μm) at a flow rate of 20 mL/min.

Example 1. 6-(cyclopropanecarboxamido)-4-((2-methoxy-3-(1-(methyl-d3)-1H-1,2,4-triazol-3-yl)phenyl)amino)-N-(methyl-d3)pyridazine-3-carboxamide (1)

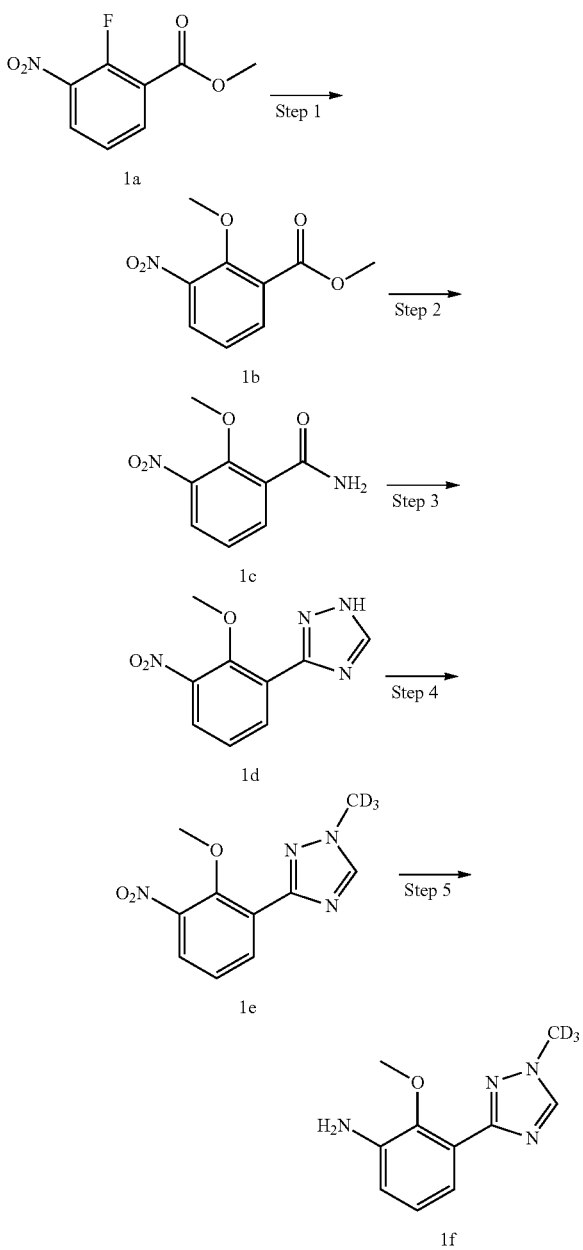 [SMILES: COC(=O)c1cccc([N+](=O)[O-])c1F ; COC(=O)c1cccc([N+](=O)[O-])c1OC ; COc1c(C(N)=O)cccc1[N+](=O)[O-] ; COc1c(-c2nc[nH]n2)cccc1[N+](=O)[O-] ; [2H]C([2H])([2H])n1cnc(-c2cccc([N+](=O)[O-])c2OC)n1 ; [2H]C([2H])([2H])n1cnc(-c2cccc(N)c2OC)n1]

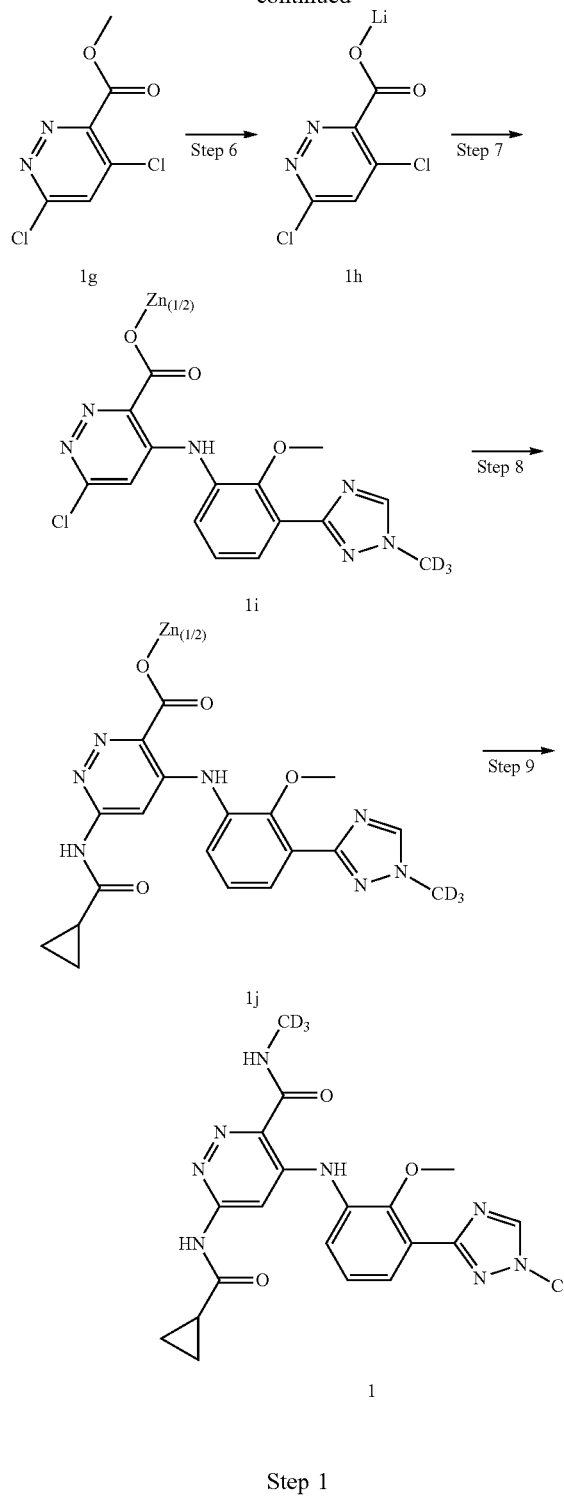

sulfate and filtered. The filtrate was concentrated to dryness under reduced pressure to obtain the target compound 1b (10 g, solid) with a yield of 98%.

MS m/z (ESI): 212 [M+1]

Step 2

2-Methoxy-3-nitrobenzamide (1c)

To a solution of methyl 2-methoxy-3-nitrobenzoate 1b (10 g, 47 mmol) in methanol (40 mL) at room temperature was added ammonium hydroxide (20 mL). After stirring at room temperature for 48 hours, the solvent was removed under reduced pressure to obtain the target compound 1c (crude, 10 g, solid). The crude product was used in the next step without further purification.

MS m/z (ESI): 197 [M+1]

Step 3

3-(2-Methoxy-3-nitrophenyl)-1H-1,2,4-triazole (1d)

A solution of 2-methoxy-3-nitrobenzamide 1c (10 g, 51 mmol) in N,N-dimethylformamide dimethyl acetal (50 mL) was heat to 95° C. and stirred for 2 hours. After cooling to room temperature, the solvent was removed under reduced pressure and the residue was dissolved in ethanol (30 mL) to obtain solution A. Hydrazine hydrate (25 mL) was slowly added to a mixture of acetic acid (35 mL) and ethanol (150 mL) at 0° C., followed by addition of solution A. After gradually warming to room temperature and stirring for 12 hours, the solvent was removed under reduced pressure. The residue was dispersed in water (400 mL) and filtered. The obtained solid was washed with water and dried to give the target compound 1d (6 g, solid) with a yield of 55%.

MS m/z (ESI): 221 [M+1]

Step 4

3-(2-Methoxy-3-nitrophenyl)-1-(methyl-d3)-1H-1,2,4-triazole (1e)

To a mixture of 3-(2-methoxy-3-nitrophenyl)-1-(methyl-d3)-1H-1,2,4-triazole 1d (1.2 g, 5.3 mmol), potassium carbonate (2.2 g, 16 mmol) and N,N-dimethylformamide (10 mL) was added deuterated iodomethane (1 g, 6.9 mmol). After stirring at room temperature for 12 hours, the resulting solution was purified by reversed phase prep-HPLC to obtain the target compound 1e (530 mg, solid) with a yield of 42%.

MS m/z (ESI): 238 [M+1]

Step 5

2-Methoxy-3-(1-(methyl-d3)-1H-1,2,4-triazol-3-yl) aniline (1f)

To a solution of 3-(2-methoxy-3-nitrophenyl)-1-(methyl-d3)-1H-1,2,4-triazole 1e (530 mg, 1.61 mmol) in methanol (10 mL) was added 10% palladium on carbon (50 mg). The reaction mixture was stirred under a hydrogen atmosphere for 12 hours and then filtered. The filtrate was concentrated to dryness under reduced pressure to obtain the target product 1f (430 mg, solid). The product was used in the next reaction without further purification.

MS m/z (ESI): 208 [M+1]

Step 6

Lithium 4,6-dichloropyridazine-3-carboxylate (1h)

To a mixture of methyl 4,6-dichloropyridazine-3-carboxylate 1g (5 g, 24.15 mmol), diisopropylethylamine (9.4 g, 72.5 mmol), acetonitrile (13.5 mL) and water (3.25 mL) was added lithium bromide (6.3 g, 72.5 mmol). The resulting mixture was stirred at room temperature for 12 hours and filtered. The resulting solid was washed with acetonitrile (8 mL) and dried under vacuum to give the target compound 1h (4.53 g, solid) with a yield of 90%.

MS m/z (ESI): 193 [M+1]

Step 7

Zinc 6-chloro-4-((2-methoxy-3-(1-(methyl-d3)-1H-1,2,4-triazol-3-yl)phenyl)amino)pyridazine-3-carboxylate (1i)

To a mixture of lithium 4,6-dichloropyridazine-3-carboxylate 1h (380 mg, 1.9 mmol), 2-methoxy-3-(1-(methyl-d3)-1H-1,2,4-triazol-3-yl)aniline 1f (471 mg, 2.27 mmol), isopropanol (0.5 mL) and water (5 mL) was added zinc acetate (350 mg, 1.9 mmol) at room temperature. The mixture was heated to 65° C. and stirred for 12 hours. After cooling to room temperature, the reaction mixture was diluted with water (30 mL), stirred for 30 minutes and filtered. The solid was washed with water (2×30 mL) and tetrahydrofuran (2×30 mL) and dried under vacuum to give the target compound 1i (490 mg, solid) with a yield of 71%.

MS m/z (ESI): 364 [M+1]

Step 8

Methyl 6-(cyclopropanecarboxamido)-4-((2-methoxy-3-(1-(methyl-d3)-1H-1,2,4-triazol-3-yl)phenyl)amino)pyridazine-3-carboxylate (1j)

To a mixture of zinc 6-chloro-4-((2-methoxy-3-(1-(methyl-d3)-1H-1,2,4-triazol-3-yl)phenyl)amino) pyridazine-3-carboxylate 1i (490 mg, 1.15 mmol), cyclopropanecarboxamide (300 mg, 3.45 mmol), (2R)-1-[(1R)-1-[bis(1,1-dimethylethyl)phosphino]ethyl]-2-(dicyclohexylphosphino)ferrocene (63 mg, 0.115 mmol), palladium acetate (25 mg, 0.0575 mmol), toluene (9 mL) and acetonitrile (5 mL) were added potassium carbonate (320 mg, 7.8 mmol) and 1,8-diazabicycloundec-7-ene (180 mg, 1.5 mmol) sequentially. The resulting mixture was stirred at 80° C. for 72 hours under nitrogen. After cooling to room temperature, the solvent was removed under reduced pressure and the residue was purified by reversed phase prep-HPLC to give the target compound 1j (560 mg, solid) with a yield of 99%.

MS m/z (ESI): 413 [M+1]

Step 9

6-(Cyclopropanecarboxamido)-4-((2-methoxy-3-(1-(methyl-d3)-1H-1,2,4-triazol-3-yl)phenyl)amino)-N-(methyl-d3)pyridazine-3-carboxamide (1)

A mixture of methyl 6-(cyclopropanecarboxamido)-4-((2-methoxy-3-(1-(methyl-d3)-1H-1,2,4-triazol-3-yl)phenyl) amino)pyridazine-3-carboxylate 1j (280 mg, 0.68 mmol), deuterated methylamine hydrochloride (60 mg, 0.81 mmol), 1-ethyl-3-(3-dimethylaminopropyl)carbodiimide hydrochloride (181 mg, 0.95 mmol), 1-hydroxybenzotriazole (53 mg, 0.34 mmol), acetonitrile (3 mL), N-methylpyrrolidone and N-methylimidazole (41 mg, 0.5 mmol) was heated to 65° C. and stirred for 1 hour. After cooling to room temperature, the solvent was removed under reduced pressure, and the residue was purified by reversed phase prep-HPLC to give the target compound 1 (44 mg, solid) with a yield of 15%.

MS m/z (ESI): 429 [M+1]

$^1$H NMR (400 MHz, DMSO-$d_6$) δ11.32 (s, 1H), 10.97 (s, 1H), 9.13 (s, 1H), 8.56 (s, 1H), 8.15 (s, 1H), 7.65 (dd, J=7.8, 1.5 Hz, 1H), 7.54-7.46 (m, 1H), 7.32-7.22 (m, 1H), 3.72 (s, 3H), 2.12-2.03 (m, 1H), 0.88-0.73 (m, 4H).

Example 2. 6-(cyclopropanecarboxamido)-4-((2-methoxy-3-(1-(methyl-$d_3$)-1H-1,2,4-triazol-3-yl) phenyl)amino)-N-methylpyridazine-3-carboxamide (2)

Compound 2 was synthesized according to the methods for Example 1 except that methylamine hydrochloride (CH$_3$NH$_2$.HCl) was used in step 9 instead of deuterated methylamine hydrochloride (CD$_3$NH$_2$.HCl).

MS m/z (ESI): 426 [M+1]

$^1$H NMR (400 MHz, DMSO-$d_6$) δ 11.32 (s, 1H), 10.97 (s, 1H), 9.22-9.11 (m, 1H), 8.56 (s, 1H), 8.15 (s, 1H), 7.66 (dd, J=7.8, 1.5 Hz, 1H), 7.51 (dd, J=8.0, 1.5 Hz, 1H), 7.31-7.22 (m, 1H), 3.72 (s, 3H), 2.86 (d, J=4.8 Hz, 3H), 2.15-2.01 (m, 1H), 0.87-0.75 (m, 4H).

Example 3. 6-(cyclopropanecarboxamido)-4-((2-(methoxy-$d_3$)-3-(1-methyl-1H-1,2,4-triazol-3-yl) phenyl)amino)-N-methylpyridazine-3-carboxamide (3)

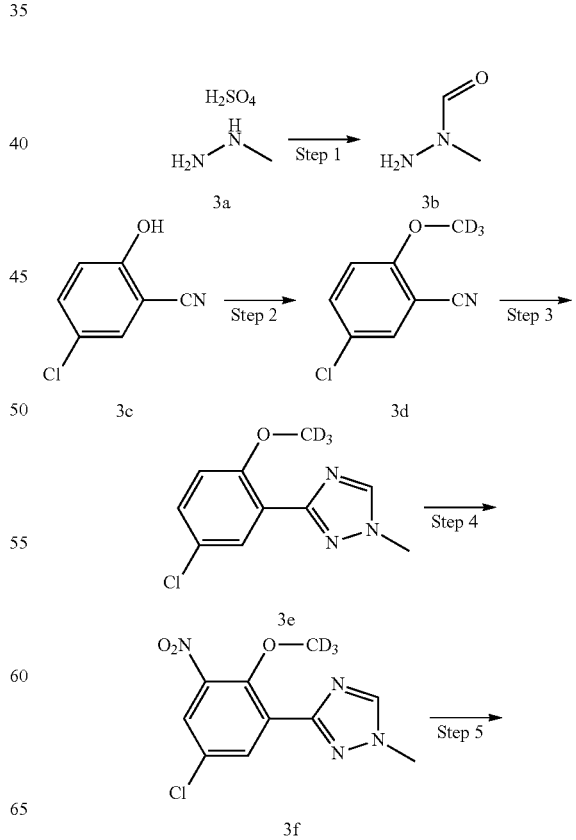

-continued

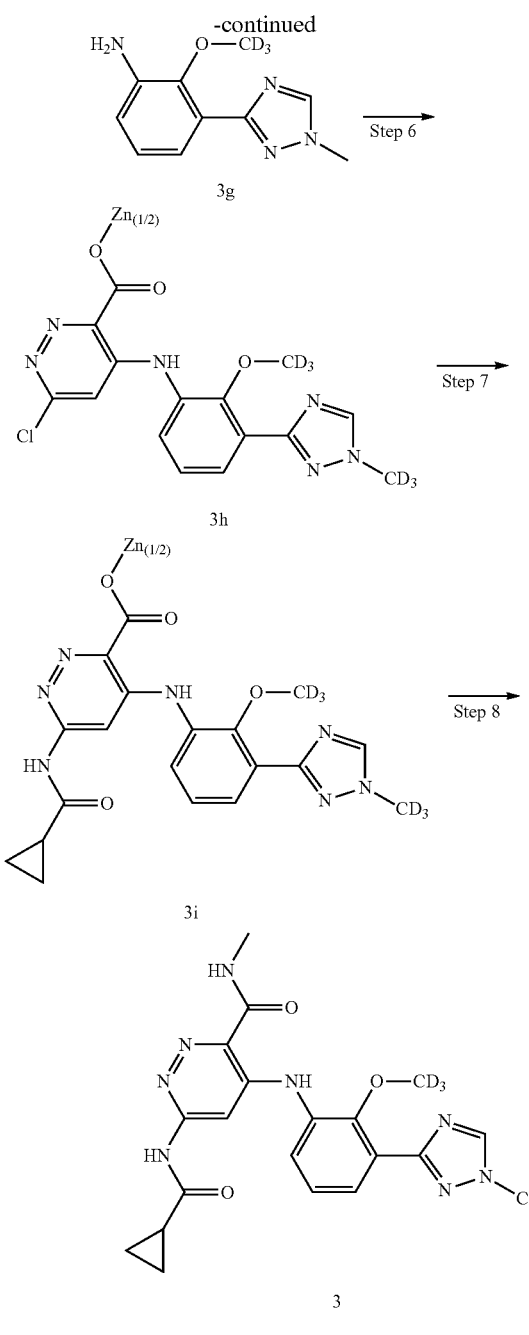

Step 1

N-methylformohydrazide

To a solution of methylhydrazine sulfate 3a (40 g, 277 mmol) in methanol (250 mL) at room temperature was added sodium methoxide (100 g, 554 mmol). The resulting mixture was stirred for 24 hours and filtered. The filtrate was then added with methyl formate (17 g, 277 mmol) and stirred at room temperature for 18 hours. The solvent was removed under reduced pressure to give the target compound 5b (22 g, crude). The crude product was directly used in the next step without further purification.

MS m/z (ESI): 75 [M+1]

Step 2

5-chloro-2-(methoxy-d3)benzonitrile (3d)

To a mixture of 5-chloro-2-hydroxybenzonitrile 3c (4 g, 26 mmol), potassium carbonate (7.3 g, 53 mmol) and N,N-dimethylformamide (30 mL) was added deuterated methyl iodide at room temperature (10 g, 78 mmol). The resulting mixture was heated to 70° C. and stirred for 12 hours. After cooling to room temperature, the reaction mixture was diluted with water (200 mL) and extracted with ethyl acetate (2×100 mL). The combined organic phases were washed with saturated brine (2×100 mL), dried over anhydrous sodium sulfate, filtered and concentrated to dryness under reduced pressure to give the target compound 3d (4.3 g, solid) with a yield of 97%.

MS m/z (ESI): 171 [M+1 ]

Step 3

3-(5-chloro-2-(methoxy-d3)phenyl)-1-methyl-1H-1,2,4-triazole sulfate (3e)

To a solution of potassium tert-butoxide (11.3 g, 101 mmol) in tetrahydrofuran (30 mL) at 0° C. were added 5-chloro-2-(methoxy-d3)benzonitrile 3d (4.3 g, 25.3 mmol) and a solution of N-methylformylhydrazide (4.1 g, 58 mmol) in tetrahydrofuran (20 mL) sequentially. After stirring at room temperature for 12 hours, the mixture was added with water (50 mL), heated to 40° C. and stirred for 40 minutes. After cooling to room temperature, the organic phase was separated, washed with saturated brine (40 mL), dried over anhydrous sodium sulfate, filtered and concentrated to dryness. The residue was dissolved in ethyl acetate (40 mL). The resulting solution was slowly added with concentrated sulfuric acid (5 g) at room temperature and stirred for 12 hours. The mixture was then filtered and dried to give the target compound 3e (5.6 g, solid) with a yield of 83%.

MS m/z (ESI): 227 [M+1]

Step 4

3-(5-Chloro-2-(methoxy-$d_3$)-3-nitrophenyl)-1-methyl-1H-1,2,4-triazole (3f)

To a solution of 3-(5-chloro-2-(methoxy-d3)phenyl)-1-methyl-1H-1,2,4-triazole sulfate 3e (5.6 g, 24.7 mmol) in sulfuric acid (25 g) was added nitric acid (2 g) at 0° C. The resulting solution was gradually warmed to room temperature, stirred for 12 hours, and then cooled to 0° C. again. Water (67 mL) and methanol (47 mL) were added to the solution at 0° C., then warmed to room temperature and stirred for 1 hour. The solution was heated to 40° C. and to which ammonium hydroxide (42 mL) was added. The solution was cooled to 20° C., stirred for 2 hours, and then filtered. The solid was washed with water (2×30 mL) and dried under vacuum to give the target compound 3f (3.37 g, solid) with a yield of 50%.

MS m/z (ESI): 272 [M+1]

Step 5

2-(Methoxy-d₃)-3-(1-methyl-1H-1,2,4-triazol-3-yl)aniline (3g)

To a solution of 3-(5-chloro-2-(methoxy-d₃)-3-nitrophenyl)-1-methyl-1H-1,2,4-triazole 3f (3.37 g, 12.25 mmol) in methanol (10 mL) were added 10% palladium on carbon (400 mg) and sodium bicarbonate (1.6 g, 25 mmol). The resulting mixture was stirred under a hydrogen atmosphere for 12 hours and then filtered. The filtrate was concentrated to dryness under reduced pressure and the residue was dissolved in dichloromethane (25 mL). The resulting mixture was filtered, and the filtrate was concentrated to dryness under reduced pressure to give the target compound 3g (2.35 g, solid) with a yield of 92%.

MS m/z (ESI): 208 [M+1]

Step 6

Zinc 6-chloro-4-((2-(methoxy-d₃)-3-(1-methyl-1H-1,2,4-triazol-3-yl)phenyl)amino)pyridazine-3-carboxylate (3h)

To a mixture of lithium 4,6-dichloropyridazine-3-carboxylate 1h (3 g, 15.1 mmol), 2-(methoxy-d₃)-3-(1-methyl-1H-1,2,4-triazol-3-yl)aniline 3g (2.35 g, 11.3 mmol), isopropanol (2.5 mL) and water (18 mL) at room temperature was added zinc acetate (2.5 g, 13.6 mmol). The mixture was heated to 65° C. and stirred for 12 hours. After cooling to room temperature, the mixture was diluted with water (20 mL), stirred for 30 minutes and filtered. The solid was washed with water (2×30 mL) and tetrahydrofuran (2×30 mL) and dried under vacuum to give the target compound 3h (4.3 g, solid) with a yield of 100%.

MS m/z (ESI): 364 [M+1]

Step 7

Methyl 6-(cyclopropanecarboxamido)-4-((2-(methoxy-d₃)-3-(1-methyl-1H-1,2,4-triazol-3-yl)phenyl)amino)pyridazine-3-carboxylate (3i)

A mixture of zinc 6-chloro-4-((2-(methoxy-d₃)-3-(1-methyl-1H-1,2,4-triazol-3-yl)phenyl)amino)pyridazine-3-carboxylate 3h (4.3 g, 11 mmol), cyclopropanecarboxamide (2.4 g, 27.56 mmol), (2R)-1-[(1R)-1-[bis(1,1-dimethylethyl)phosphino]ethyl]-2-(dicyclohexylphosphino)ferrocene (600 mg, 1.1 mmol), palladium acetate (125 mg, 0.55 mmol), toluene (34 mL), acetonitrile (17 mL), potassium carbonate (3.1 g, 22 mmol) and 1,8-diazabicycloundec-7-ene (1.7 g, 11 mmol) was heated to 80° C. under a nitrogen atmosphere and stirred for 12 hours. After cooling to room temperature, the mixture was added with aqueous acetic acid (50%, 17 mL) and glacial acetic acid (40 mL) sequentially. After stirring at room temperature for 1 hour, the resulting homogenous mixture was washed with petroleum ether (2×20 mL). Water (50 mL) was added, and the mixture was aged at room temperature for 4 hours and then filtered. The solid was washed with an acetonitrile aqueous solution (50%, 20 mL) and acetonitrile (20 mL) sequentially, and then dried under vacuum at 65° C. for 30 minutes to give the target product 3i (3 g, solid) with a yield of 66%.

MS m/z (ESI): 413 [M+1]

Step 8

6-(Cyclopropanecarboxamido)-4-((2-(methoxy-d₃)-3-(1-methyl-1H-1,2,4-triazol-3-yl)phenyl)amino)-N-methylpyridazine-3-carboxamide A mixture of methyl 6-(cyclopropanecarboxamido)-4-((2-(methoxy-d₃)-3-(1-methyl-1H-1,2,4-triazol-3-yl)phenyl)amino)pyridazine-3-carboxylate 3i (1.5 g, 3.38 mmol), methylamine hydrochloride (280 mg, 4.0 mmol), 1-ethyl-3-(3-dimethylaminopropyl)carbodiimide hydrochloride (900 mg, 4.73 mmol), 1-hydroxybenzotriazole (230 mg, 1.7 mmol), acetonitrile (3 mL), N-methylpyrrolidone (3 mL) and N-methylimidazole (200 mg, 2.4 mmol) was heated to 65° C. and stirred for 12 hours. After the reaction was completed, the reaction was quenched with water (1.5 mL) and acetonitrile (4.5 mL). The resulting mixture was aged at 65° C. for 1 hour and at 0° C. for 3 hours, and then filtered. The solid was sequentially washed with an acetonitrile aqueous solution (33%, 4.5 mL) and acetonitrile (4.5 mL), and dried under vacuum at 65° C. for 8 hours to give the target product 3 (811 mg, solid) with a yield of 56%.

MS m/z (ESI): 426 [M+1]

¹H NMR (400 MHz, DMSO-d₆) δ 11.32 (s, 1H), 10.97 (s, 1H), 9.24-9.08 (m, 1H), 8.57 (s, 1H), 8.15 (s, 1H), 7.66 (dd, J=7.8, 1.5 Hz, 1H), 7.52 (dd, J=7.9, 1.5 Hz, 1H), 7.33-7.20 (m, 1H), 3.96 (s, 3H), 2.87 (d, J=4.8 Hz, 3H), 2.14-2.01 (m, 1H), 0.91-0.73 (m, 4H).

Compound 3 could be converted into an HCl salt via the following procedure:

To a reaction flask were added 3 (5.00 g, 11.752 mmol) and DMSO (27 mL). The resulting mixture was heated to 50-55° C. while stirring until the solid was fully dissolved to a homogenous solution. The mixture was then added with concentrated hydrochloric acid (36%-38%, 1.18 g), followed by water (3 mL) and crystal seed (25 mg). The resulting mixture was stirred at 50-55° C. for 0.5 h, cooled to 35-40° C., added with isopropanol (60 mL) dropwise over 0.5-1.0 h, and stirred at 35-40° C. for 0.5 h. The mixture was slowly cooled to 20-25° C. over 1 h, stirred overnight, and then filtered. The filtered cake was washed with isopropanol (2×15 mL) and dried under reduced pressure at 65° C. overnight to give a mono-HCl salt of 3 (4.5 g, solid) with a yield of 83%.

MS m/z (ESI): 426 [M+1]

¹H NMR (400 MHz, DMSO-d₆) δ 13.72 (brs, 1H), 12.13 (s, 1H), 11.40 (s, 1H), 9.22 (q, J=4.5 Hz, 1H), 8.87 (s, 1H), 8.00 (s, 1H), 7.78 (dd, J=7.9, 1.5 Hz, 1H), 7.61 (dd, J=8.0, 1.4 Hz, 1H), 7.35 (t, J=7.9 Hz, 1H), 4.01 (s, 3H), 2.89 (d, J=4.8 Hz, 3H), 2.14-2.00 (m, 1H), 1.00-0.84 (m, 4H).

Example 4. 6-(cyclopropanecarboxamido)-4-((2-(methoxy-d₃)-3-(1-methyl-1H-1,2,4-triazol-3-yl)phenyl)amino)-N-(methyl-d₃)pyridazine-3-carboxamide (4)

Compound 4 was synthesized according to the methods for Example 3 except that deuterated methylamine hydrochloride (CD₃NH₂—HCl) was used in step 8 instead of methylamine hydrochloride (CH₃NH₂—HCl).

MS m/z (ESI): 429 [M+1]

¹H NMR (400 MHz, DMSO-d₆) δ11.32 (s, 1H), 10.98 (s, 1H), 9.14 (s, 1H), 8.57 (s, 1H), 8.15 (s, 1H), 7.66 (dd, J=7.8, 1.6 Hz, 1H), 7.52 (dd, J=7.9, 1.5 Hz, 1H), 7.32-7.21 (m, 1H), 3.96 (s, 3H), 2.14-2.03 (m, 1H), 0.89-0.75 (m, 4H).

Example 5. (S)-6-(2,2-difluorocyclopropane-1-carboxamido)-4-((2-methoxy-3-(1-methyl-1H-1,2,4-triazol-3-yl)phenyl)amino)-N-(methyl-d₃)pyridazine-3-carboxamide (5)

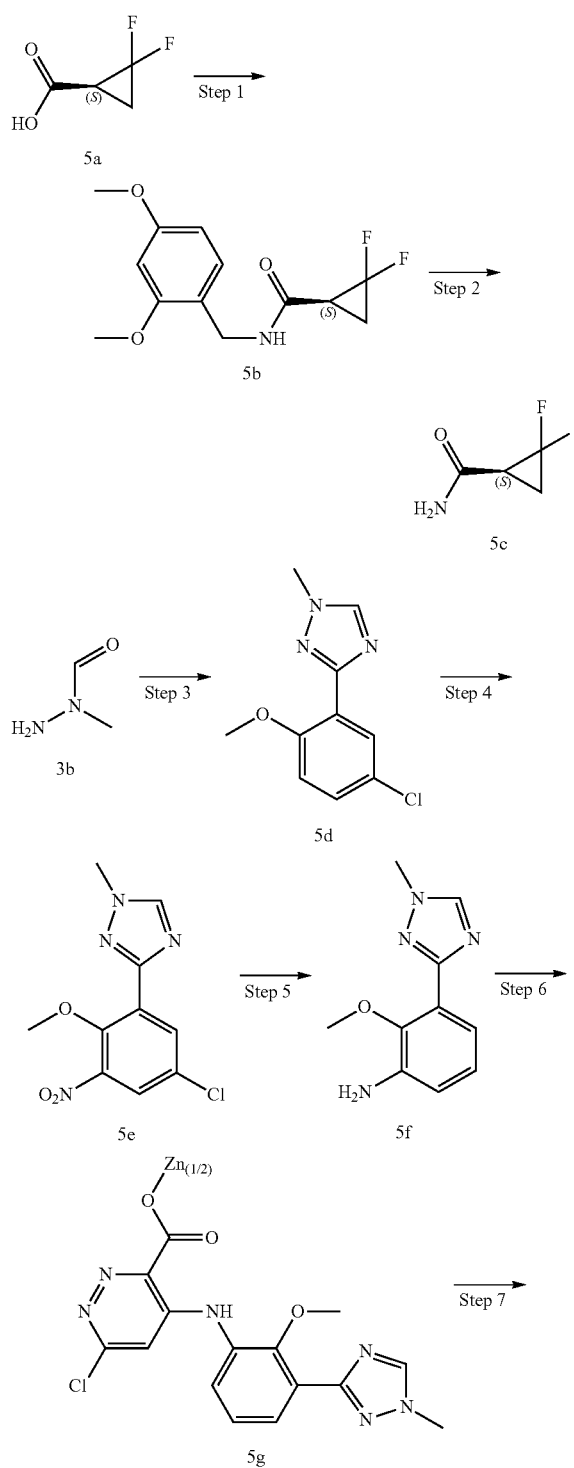

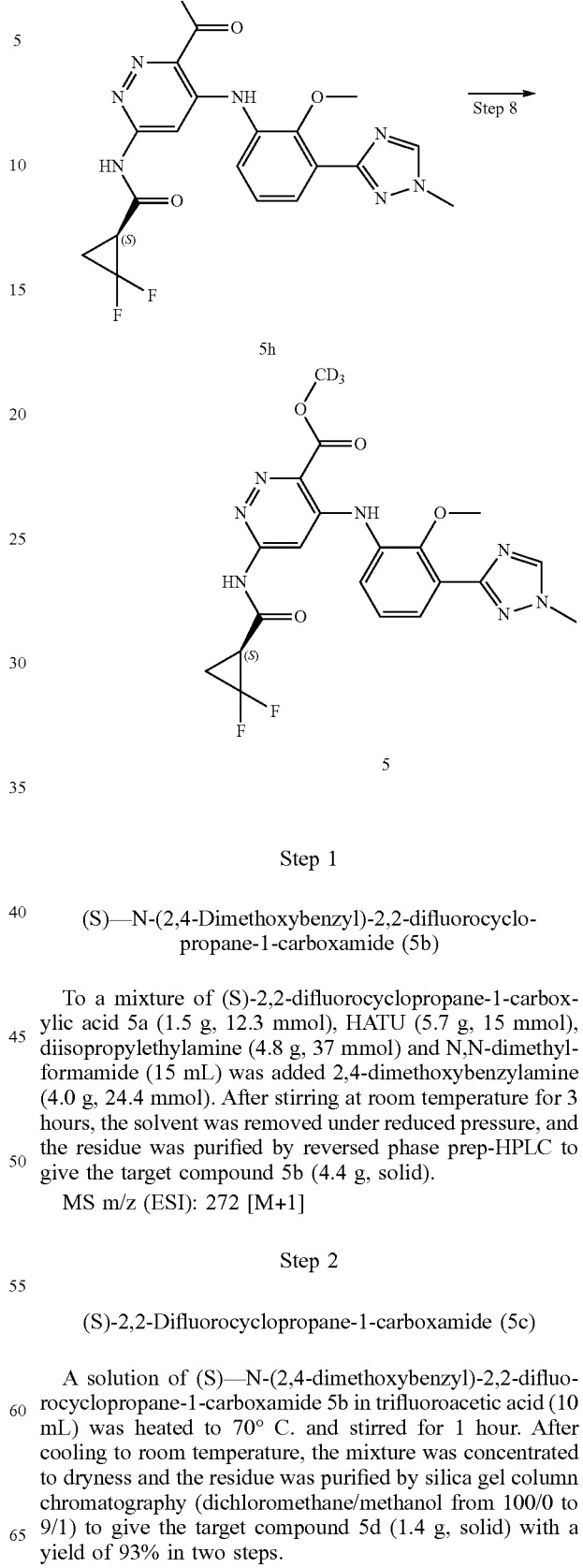

Step 1

(S)—N-(2,4-Dimethoxybenzyl)-2,2-difluorocyclopropane-1-carboxamide (5b)

To a mixture of (S)-2,2-difluorocyclopropane-1-carboxylic acid 5a (1.5 g, 12.3 mmol), HATU (5.7 g, 15 mmol), diisopropylethylamine (4.8 g, 37 mmol) and N,N-dimethylformamide (15 mL) was added 2,4-dimethoxybenzylamine (4.0 g, 24.4 mmol). After stirring at room temperature for 3 hours, the solvent was removed under reduced pressure, and the residue was purified by reversed phase prep-HPLC to give the target compound 5b (4.4 g, solid).

MS m/z (ESI): 272 [M+1]

Step 2

(S)-2,2-Difluorocyclopropane-1-carboxamide (5c)

A solution of (S)—N-(2,4-dimethoxybenzyl)-2,2-difluorocyclopropane-1-carboxamide 5b in trifluoroacetic acid (10 mL) was heated to 70° C. and stirred for 1 hour. After cooling to room temperature, the mixture was concentrated to dryness and the residue was purified by silica gel column chromatography (dichloromethane/methanol from 100/0 to 9/1) to give the target compound 5d (1.4 g, solid) with a yield of 93% in two steps.

MS m/z (ESI): 122 [M+1]

Step 3

3-(5-Chloro-2-methoxyphenyl)-1-methyl-1H-1,2,4-triazole (5d)

To a solution of potassium tert-butoxide (34 g, 290 mmol) in tetrahydrofuran (200 mL) at 0° C. were added 5-chloro-2-methoxy-benzonitrile (20 g, 120 mmol) and methylformyl hydrazide 3b (22 g, crude) sequentially. After stirring at room temperature for 72 hours, water (500 mL) was added, and the mixture was extracted with ethyl acetate (3×300 mL). The organic phases are combined, washed with saturated brine (2×300 mL), dried over anhydrous sodium sulfate, filtered and concentrated to dryness under reduced pressure to give the target compound 5d (17.1 g, solid) with a yield of 88%.

MS m/z (ESI): 224 [M+1]

Step 4

3-(5-Chloro-2-methoxy-3-nitrophenyl)-1-methyl-1H-1,2,4-triazole (5e)

To a solution of 3-(5-chloro-2-methoxyphenyl)-1-methyl-1H-1,2,4-triazole 5d (16.13 g, 72 mmol) in concentrated sulfuric acid (72 g) was added concentrated nitric acid (8.5 g, 87 mmol) at 0° C. After stirring for 2 hours, the resulting solution was added to a mixture of water (250 g) and methanol (150 g) at 0° C. The mixture was then adjusted to pH>7 with ammonium hydroxide and filtered. The solid was washed with water (2×100 mL) and purified by silica gel column chromatography (petroleum ether/ethyl acetate from 100/0 to 3/7) to give the target product 5e (17.1 g, solid) with a yield of 88%.

MS m/z (ESI): 269 [M+1]

Step 5

2-Methoxy-3-(1-methyl-1H-1,2,4-triazol-3-yl)aniline (5f)

To a solution of 3-(5-chloro-2-methoxyphenyl)-1-methyl-1H-1,2,4-triazole 5e (17 g, 63 mmol) in methanol were added 10% palladium on carbon (3 g) and sodium bicarbonate (10.5 g, 126 mmol). The reaction was stirred under a hydrogen atmosphere for 5 hours and then filtered. The filtrate was concentrated to dryness under reduced pressure and the residue was purified by reversed phase prep-HPLC to give the target compound 5f (8.8 g, solid) with a yield of 68%.

MS m/z (ESI): 205 [M+1]

Step 6

Zinc 6-chloro-4-((2-methoxy-3-(1-methyl-1H-1,2,4-triazol-3-yl)phenyl)amino)pyridazine-3-carboxylate (5g)

To a mixture of lithium 4,6-dichloropyridazine-3-carboxylate 1h (4.53 g, 22.87 mmol), 2-methoxy-3-(1-methyl-1H-1,2,4-triazol-3-yl)aniline 5f (5.6 g, 27.44 mmol), isopropanol (4.5 mL) and water (34 mL) was added zinc acetate (4.2 g, 22.87 mmol). The resulting mixture was heated to 65° C. and stirred for 12 hours. After cooling to room temperature, the mixture was diluted with water (30 mL), aged for 30 minutes and then filtered. The solid was washed with water (2×30 mL) and tetrahydrofuran (2×30 mL) and dried under vacuum to give the target compound 5g (7.6 g, solid) with a yield of 93%.

MS m/z (ESI): 361 [M+1]

Step 7

Zinc (S)-6-(2,2-difluorocyclopropane-1-carboxamido)-4-((2-methoxy-3-(1-methyl-1H-1,2,4-triazol-3-yl)phenyl)amino)pyridazine-3-carboxylate (5h)

A mixture of zinc 6-chloro-4-((2-methoxy-3-(1-methyl-1H-1,2,4-triazol-3-yl)phenyl) amino)pyridazine-3-carboxylate 5g (1.6 g, 3.93 mmol), (S)-2,2-difluorocyclopropane-1-carboxamide 5c (1.2 g, 9.8 mmol), (2R)-1-[(1R)-1-[bis(1,1-dimethylethyl)phosphino]ethyl]-2-(dicyclohexylphosphino) ferrocene (220 mg, 0.393 mmol), palladium acetate (44 mg, 0.196 mmol), toluene (18 mL), acetonitrile (11 mL), potassium carbonate (1.1 g, 7.8 mmol) and 1,8-diazabicycloundec-7-ene (600 mg, 3.93 mmol) was stirred at 80° C. for 72 hours under a nitrogen atmosphere. After cooling to room temperature, the mixture was diluted with acetic acid (27 mL) and water (9 mL), and the resulting solution was washed with petroleum ether (2×30 mL). Water (50 mL) was then added and left for 3 hours. The mixture was filtered and the solid was dried under vacuum to give the target compound 5h (1.1 g, solid) with a yield of 62%.

MS m/z (ESI): 446 [M+1]

Step 8

(S)-6-(2,2-difluorocyclopropane-1-carboxamido)-4-((2-methoxy-3-(1-methyl-1H-1,2,4-triazol-3-yl)phenyl)amino)-N-(methyl-$d_3$)pyridazine-3-carboxamide To a mixture of zinc (S)-6-(2,2-difluorocyclopropane-1-carboxamido)-4-((2-methoxy-3-(1-methyl-1H-1,2,4-triazol-3-yl)phenyl)amino)pyridazine-3-carboxylate 5h (1.1 g, 2.46 mmol), deuterated methylamine hydrochloride (210 mg, 2.95 mmol), 1-ethyl-3-(3-dimethylaminopropyl)carbodiimide hydrochloride (660 mg, 3.44 mmol), 1-hydroxybenzotriazole (190 mg, 1.23 mmol), acetonitrile (6 mL) and N-methylpyrrolidone (6 mL) was added N-methylimidazole (141 mg, 1.72 mmol). The reaction mixture was heated to 65° C. and stirred for 1 hour. After cooling to room temperature, the mixture was concentrated to dryness under reduced pressure and the residue was purified by reversed phase prep-HPLC to give the target compound 5 (420 mg, solid) with a yield of 37%.

MS m/z (ESI): 462 [M+1]
$^1$H NMR (400 MHz, DMSO-$d_6$) δ 11.52 (s, 1H), 11.01 (s, 1H), 9.18 (s, 1H), 8.58 (s, 1H), 8.09 (s, 1H), 7.67 (dd, J=7.8, 1.6 Hz, 1H), 7.53 (dd, J=7.9, 1.5 Hz, 1H), 7.33-7.23 (m, 1H), 3.95 (s, 3H), 3.73 (s, 3H), 3.13-2.97 (m, 1H), 2.10-1.95 (m, 2H).

Example 6. (S)-6-(2,2-difluorocyclopropane-1-carboxamido)-4-((2-methoxy-3-(1-methyl-1H-1,2,4-triazol-3-yl)phenyl)amino)-N-methylpyridazine-3-carboxamide (6)

Compound 6 was synthesized according to the procedures of Example 5 except deuterated methylamine hydrochloride (CD$_3$NH$_2$—HCl) in step 8 was replaced by methylamine hydrochloride (CH$_3$NH$_2$—HCl).

MS m/z (ESI): 459 [M+1]

¹H NMR (400 MHz, DMSO-d₆) δ 11.52 (s, 1H), 11.01 (s, 1H), 9.20 (d, J=4.8 Hz, 1H), 8.56 (s, 1H), 8.09 (s, 1H), 7.67 (dd, J=7.8, 1.6 Hz, 1H), 7.52 (dd, J=8.0, 1.5 Hz, 1H), 7.33-7.23 (m, 1H), 3.95 (s, 3H), 3.73 (s, 3H), 3.11-2.98 (m, 1H), 2.86 (d, J=4.8 Hz, 3H), 2.10-1.94 (m, 2H).

Example 7. (R)-6-(2,2-difluorocyclopropane-1-carboxamido)-44(2-methoxy-3-(1-methyl-1H-1,2,4-triazol-3-yl)phenyl)amino)-N-(methyl-d3) pyridazine-3-carboxamide (7)

Compound 7 was synthesized according to the procedures of Example 5 except (S)-2,2-difluorocyclopropane-1-carboxylic acid (5a) in step 1 was replaced by (R)-2,2-difluorocyclopropane-1-carboxylic acid.

MS m/z (ESI): 462 [M+1]

¹H NMR (400 MHz, DMSO-d₆) δ 11.52 (s, 1H), 11.01 (s, 1H), 9.18 (s, 1H), 8.56 (s, 1H), 8.09 (s, 1H), 7.67 (dd, J=7.8, 1.6 Hz, 1H), 7.53 (dd, J=7.9, 1.5 Hz, 1H), 7.28 (m, 1H), 3.95 (s, 2H), 3.73 (s, 3H), 3.11-2.99 (m, 1H), 2.10-1.95 (m, 2H).

Example 8. (R)-6-(2,2-difluorocyclopropane-1-carboxamido)-44(2-methoxy-3-(1-methyl-1H-1,2,4-triazol-3-yl)phenyl)amino)-N-methylpyridazine-3-carboxamide (8)

Compound 8 was synthesized according to the procedures of Example 5 except (i) (S)-2,2-difluorocyclopropane-1-carboxylic acid (5a) in step 1 was replaced by (R)-2,2-difluorocyclopropane-1-carboxylic acid, and (ii) deuterated methylamine hydrochloride (CD₃NH₂—HCl) in step 8 was replaced by methylamine hydrochloride (CH₃NH₂—HCl).

MS m/z (ESI): 459 [M+1]

¹H NMR (400 MHz, DMSO-d₆) δ 11.52 (s, 1H), 11.01 (s, 1H), 9.27-9.16 (m, 1H), 8.56 (s, 1H), 8.09 (s, 1H), 7.67 (dd, J=7.8, 1.6 Hz, 1H), 7.52 (dd, J=8.0, 1.5 Hz, 1H), 7.33-7.24 (m, 1H), 3.95 (s, 2H), 3.73 (s, 2H), 3.11-2.99 (m, 1H), 2.86 (d, J=4.8 Hz, 3H), 2.08-1.95 (m, 2H).

Example 9. JAK2 Kinase Domain Enzymatic Activity Assay

The effect of the compounds of the present invention on the enzymatic activity of recombinant JAK2 kinase domain (JH1) is assessed by detecting the substrate phosphorylation level in a kinase reaction using the HTRF kinase assay detection kit (Cisbio, Cat. No. 62TK0PEC) (Table 1).

The experimental method is generally described below:

A reaction buffer containing the following components: an enzyme buffer (1×), 5 mM $MgCl_2$, 1 mM DTT and 0.01% Brij35 from the kit; a human recombinant JAK2 kinase domain protein (Carna Biosciences, Cat. No. 08-045) diluted to a solution of 0.15 ng/μL with the reaction buffer; a substrate reaction solution containing 2.5 μM ATP and a biotinylated tyrosine kinase substrate diluted to 0.25 μM with the reaction buffer; a detection solution containing 0.1 ng/μL $Eu^{3+}$ labeled cage antibody (Cisbio, Cat. No. 61T66KLB) and 12.5 nM streptavidin-labeled XL665 (Cisbio, Cat. No. 610SAXLB) in the reaction buffer.

The test compound is dissolved to 1 mM in DMSO, followed by a serial 4-fold dilution with DMSO to a minimum concentration of 61 nM. Each concentration is further diluted 40-fold with the reaction buffer.

To a 384-well assay plate (Corning, Cat. No. 3674) are added 4 μL of compound solution and 2 μL of JAK2 kinase solution. The mixture is incubated at room temperature for 15 minutes, and then added with 4 μL of the substrate reaction solution. After further incubation at room temperature for 30 minutes, the reaction mixture is added with an equal volume of 10 μL detection solution and allowed to stand at room temperature for 30 minutes. An Envision plate reader (Perkin Elmer) is then used to measure the progress of the reaction at 620 nm and 665 nm. The ratio of absorbances at 665 nm and 620 nm is positively correlated with the degree of substrate phosphorylation, therefore the activity of JAK2 kinase is detected. In this experiment, the group without JAK2 kinase protein is the 100% inhibition group, and the group with JAK2 kinase protein but not the test compound is the 0% inhibition group. The percentage of inhibition on JAK2 kinase activity by the test compound is calculated using the following formula:

Percentage of inhibition = 100 −

$100 * (ratio_{compound} - ratio_{100\% \ inhibition}) / (ratio_{0\% \ inhibition} - ratio_{100\% \ inhibition})$ The $IC_{50}$ value of the test compound is calculated from 8 concentration points using the XLfit software (ID Business Solutions Ltd., UK) by the following formula:

$Y = \text{Bottom} + (\text{Top} - \text{Bottom}) / (1 + 10^{\wedge}((\log IC_{50} - X) \times \text{slope factor}))$ Where Y is the percentage of inhibition, X is the logarithm of the concentration of the test compound, Bottom is the bottom plateau value of the S-shaped curve, Top is the top plateau value of the S-shaped curve, and slope factor is the slope coefficient of the curve.

Example 10. TYK2 Kinase Domain Enzymatic Activity Assay

The effect of the compounds of the present invention on the enzymatic activity of recombinant TYK2 kinase domain (JH1) is assessed by detecting the substrate phosphorylation level in a kinase reaction using the HTRF kinase assay detection kit (Cisbio, Cat. No. 62TKOPEC) (Table 1).

The experimental method is generally described below:

A reaction buffer containing the following components: an enzyme buffer (1×), 5 mM $MgCl_2$, 1 mM DTT, 10 nM SEB (Cisbio, Cat. No. 61SEBALB), 0.625 mM EGTA and 0.01% Brij35 from the kit; a human recombinant TYK2 kinase (JH1) domain protein (Carna Biosciences, Cat. No. 08-147) diluted to a solution of 0.25 ng/μL with the reaction buffer; a substrate reaction solution containing 11.25 μM ATP and a biotinylated tyrosine kinase substrate diluted to 0.5 μM with the reaction buffer; a detection solution containing 0.1 ng/μL $Eu^{3+}$ labeled cage antibody (Cisbio, Cat. No. 61T66KLB) and 25 nM streptavidin-labeled XL665 (Cisbio, Cat. No. 610SAXLB) in the reaction buffer.

The test compound is dissolved to 1 mM in DMSO, followed by a serial 4-fold dilution with DMSO to a minimum concentration of 61 nM. Each concentration is further diluted 40-fold with the reaction buffer.

To a 384-well assay plate (Corning, Cat. No. 3674) are added 4 μL of compound solution and 2 μL of TYK2 kinase solution. The mixture is incubated at room temperature for 15 minutes, and then added with 4 μL of the substrate reaction solution. After further incubation at room temperature for 40 minutes, the reaction mixture is added with an equal volume of 10 μL detection solution and allowed to stand at room temperature for 30 minutes. An Envision plate reader (Perkin Elmer) is then used to measure the progress of the reaction at 620 nm and 665 nm. The ratio of absorbances at 665 nm and 620 nm is positively correlated with the degree of substrate phosphorylation, therefore the activity of TYK2 kinase is detected. In this experiment, the group without TYK2 kinase protein is the 100% inhibition group, and the group with TYK2 kinase protein but not the test compound is the 0% inhibition group. The percentage of inhibition on TYK2 kinase activity by the test compound is calculated using the following formula:

Percentage of inhibition = 100 −
$100 * (ratio_{compound} - ratio_{100\% \, inhibition})/(ratio_{0\% \, inhibition} - ratio_{100\% \, inhibition})$ The $IC_{50}$ value of the test compound is calculated from 8 concentration points using the XLfit software (ID Business Solutions Ltd., UK) by the following formula:

$$Y = \text{Bottom} + (\text{Top} - \text{Bottom})/(1 + 10^{\wedge}((\log IC_{50} - X) \times \text{slope factor}))$$

Where Y is the percentage of inhibition, X is the logarithm of the concentration of the test compound, Bottom is the bottom plateau value of the S-shaped curve, Top is the top plateau value of the S-shaped curve, and slope factor is the slope coefficient of the curve.

Example 11. TYK2 Pseudokinase Domain Binding Assay

The binding of the compounds of the present invention to TYK2 pseudokinase domain (JH2) is determined by using a time-resolved fluorescence energy transfer (TR-FRET) biochemical assay through competition with a commercial fluorescein-labeled probe (Alexa-Fluor 647-conjugated kinase tracer 178) (Table 1).

The experimental method is generally described below:

A binding buffer contains 20 mM Hepes pH 7.5, 150 mM NaCl, 10 mM $MgCl_2$, 0.015% Brij35, 2 mM DTT, 0.625 mM EGTA and 100 mM KF. The JH2 domain of TYK2 (amino acids 556-871 within the full-length protein) is expressed and purified by at Tsinghua University protein purification and identification platform. The test compound is dissolved to 0.1 mM in DMSO, followed by a serial 4-fold dilution with DMSO to a minimum concentration of 61 nM. Each concentration is further diluted 40-fold with the reaction buffer.

To a 384-well assay plate (Corning, Cat. No. 4512) are added 5 μL of compound solution and 5 μL of TYK2 JH2 domain solution (160 nM). The mixture is incubated at room temperature for 30 minutes, and then added with 10 μL of a mixture of fluorescein-labeled probe (ThermoFisher, Cat. No. PV5593) (20 nM) and GST-Europium (Eu)-labeled antibody (Cisbio, Cat. No. 61GSTKLA) (40 ng/mL). After further incubation at room temperature for 30 minutes, the HTRF signal (ratio of fluorescence intensity at the emission wavelength of 615 nm and 665 nm for the fluorescein acceptor and the Europium donor, respectively) is measured on an Envision plate reader (Perkin Elmer). The percentage of inhibition is calculated by comparing to a positive control without the test compound and a negative control without protein according to the following formula:

$$\% \text{ of inhibition} = 100 - 100 * (signal_{compound} - signal_{negative \, control})/(signal_{positive \, control} - signal_{negative \, control})$$

The $IC_{50}$ value of the test compound is calculated from 8 concentration points using the XLfit software (ID Business Solutions Ltd., UK) by the following formula:

$$Y = \text{Bottom} + (\text{Top} - \text{Bottom})/(1 + 10^{\wedge}((\log IC_{50} - X) \times \text{slope factor}))$$

Where Y is the percentage of inhibition, X is the logarithm of the concentration of the test compound, Bottom is the bottom plateau value of the S-shaped curve, Top is the top plateau value of the S-shaped curve, and slope factor is the slope coefficient of the curve.

TABLE 1

| | $IC_{50}$ (μM) | | $IC_{50}$ (nM) |
| --- | --- | --- | --- |
| Compound No. | JAK2 Kinase Domain (JH1) | TYK2 Kinase Domain (JH1) | TYK2 Pseudokinase Domain (JH2) |
| 1 | 2.3 | 2.1 | |
| 2 | 2.2 | >10 | 5.6 |
| 3 | 3.0 | >10 | 5.7 |
| 4 | 2.3 | >10 | |
| 5 | 7.0 | 6.3 | 5.4 |
| 6 | 7.8 | 9.5 | 4.9 |
| 7 | 8.5 | >10 | |
| 8 | 7.5 | >10 | |
| Reference (BMS-986165) | 0.84 | 2.9 | 5.5 |

The compounds of the present invention have weak or low inhibiting activity toward the kinase domains of JAK2 or TYK2. Table 1 shows that Compounds 2, 3, 4, 7, and 8 had $IC_{50}$>10 μM for direct inhibition of the kinase activity, whereas the Reference compound had a lower $IC_{50}$ of 2.9 The test compounds and the reference compounds all had strong binding toward TYK2 JH2 ($IC_{50}$ in the nM range)

Example 12. Inhibition of IL-12-Induced IFN-γ Secretion in NK92 Cells

The effect of the compounds of the present invention on IFN-γ secretion induced by TYK2 in NK92 cells is evaluated by an enzyme-linked immunosorbent assay (ELISA) (Table 2).

IL-12 receptor is mainly expressed in activated T-cells, NK cells (NK92 is a NK cell line), DC cells, and B-cells. When binding to IL-12, it activates JAK2/TYK2 signal transduction pathway within NK cells and T lymphocytes, thereby inducing secretion of IFN-γ.

The experimental method is generally described below:

The test compound is dissolved to 2.5 mM in DMSO, followed by a serial 4-fold dilution with DMSO to a minimum concentration of 0.31 μM. Each concentration is further diluted 50-fold with an FBS-free MEMα medium (Gibco, Cat. No. 12561-056).

NK92 cells (Nanjing Cobioer, Cat. No. CBP60980) are cultured in a complete MEMα medium containing 12.5% FBS (Ausbian, Cat. No. VS500T), 12.5% horse serum (Gibco, Cat. No. 16050-122), 0.02 mM folic acid (Sigma, Cat No. F8758), 0.2 mM inositol (Sigma, Cat No. 17850), 0.55 mM β-mercaptoethanol (Gibco, Cat No. 21985-023), 200 U/mL IL-2 (R&D Systems, Cat No. 202-1L), and 100 U/mL penicillin (ThermoFisher, Cat No. 15140122). When covering 80-90% of the culture container surface, the cells are dispersed and plated on a 96-well plate (ThermoFisher, Cat No. 167425) with 100,000 cells per well (80 µL of the complete MEMα medium without IL-2). The 96-well plate is then incubated overnight in a 37° C./5% $CO_2$ incubator.

After overnight incubation, 10 µL of the test compound and 10 µL of 50 ng/mL IL-12 (R & D Systems, Cat. No. 219-1L) are added to each well and mix gently, and the 96-well plate is incubated in the 37° C./5% $CO_2$ incubator for additional 24 hours. The plate is centrifuged at 800 rpm for 10 minutes at room temperature and 50 µL of the supernatant from each well is transferred to another 96-well plate (Sigma, Cat No. CLS3695) coated with anti-IFN-γ antibody. The amount of IFN-γ secretion is detected following the instruction from the Human IFN-gamma DuoSet ELISA kit (R & D Systems, Cat No. DY285B). In the experiment, the group with IL-12 and the test compound being replaced with the MEMα medium is the non-stimulated control group (100% inhibition), and the group with IL-12 and 0.2% DMSO is the stimulated group (0% inhibition). The percentage of inhibition on IL-12 induced IFN-γ secretion in NK-92 cells by the test compound is calculated using the following formula:

$$\text{Percentage of inhibition} = 100 - 100 * (signal_{compound} - signal_{non-stimulated\ control}) / (signal_{stimulated\ control} - signal_{non-stimulated\ control})$$

The $IC_{50}$ value of the test compound is calculated from 8 concentration points using the XLfit software (ID Business Solutions Ltd., UK) by the following formula:

$$Y = \text{Bottom} + (\text{Top} - \text{Bottom}) / (1 + 10^{\wedge}((\log IC_{50} - X) \times \text{slope factor}))$$

Where Y is the percentage of inhibition, X is the logarithm of the concentration of the test compound, Bottom is the bottom plateau value of the S-shaped curve, Top is the top plateau value of the S-shaped curve, and slope factor is the slope coefficient of the curve.

TABLE 2

| Compound No. | $IC_{50}$ (NK92_IL12/IFN-γ) (nM) |
|---|---|
| 1 | 16 |
| 2 | 13 |
| 3 | 14 |
| 4 | 11 |
| 5 | 52 |
| 6 | 47 |
| 7 | 74 |
| 8 | 75 |
| Reference (BMS-986165) | 17 |

The compounds of the present invention had significant inhibitory effect on the secretion of IFN-γ induced by TYK2 in NK92 cells.

Example 13. In Vivo Rat PK Determination

The pharmacokinetics of Compound 3 of the present invention and the reference compound BMS-986165 were evaluated. Compound 3 has an $OCD_3$ on a benzene ring, whereas the reference compound has an $CD_3$ on an amide moiety. Methyl group is typically labile in vivo, subject to hydrolysis by amidase in the case of methylamide and to oxidative demethylation by CYPs in the case of methoxy and methyltriazole. Substituting methyl with tri-deuterated methyl improves the bioavailability and in vivo exposure of the compound and provides a better efficacy of the compound under the same dose.

Compound 3 and the reference compound in a 0.5 mg/mL solution containing 5% N,N-dimethylacetamide+20% solutol+75% saline were orally administered to three male Sprague Dawley rats at a dose of 5 mg/kg. Blood samples were collected at 0.25, 0.5, 1, 2, 4, 8 and 24 hours after administration. The concentrations of the compound in the plasma were quantified by LC-MS/MS using an API-4500 mass spectrometer. The limit of quantification (LOQ) of analysis was 1 ng/mL. The pharmacokinetic (PK) parameters were calculated by the non-compartmental method using WinNonlin and are present in Table 3. The results show that Compound 3 of the present invention had better in vivo exposures than the reference compound.

TABLE 3

| | IV (1 mpk) (n = 3) | | | PO (5 mpk) (n = 3) | | |
|---|---|---|---|---|---|---|
| Compound No. | CL (mL/min/kg) | $V_{ss}$ (L/kg) | $T_{1/2}$ (h) | $C_{max}$ (ng/mL) | $AUC_{last}$ (h*ng/mL) | F (%) |
| 3 | 12 | 1.1 | 4.3 | 971 | 6560 | 92 |
| Reference BMS-986165 | 14 | 1.5 | 3.3 | 632 | 2828 | 46 |

Figure 2:
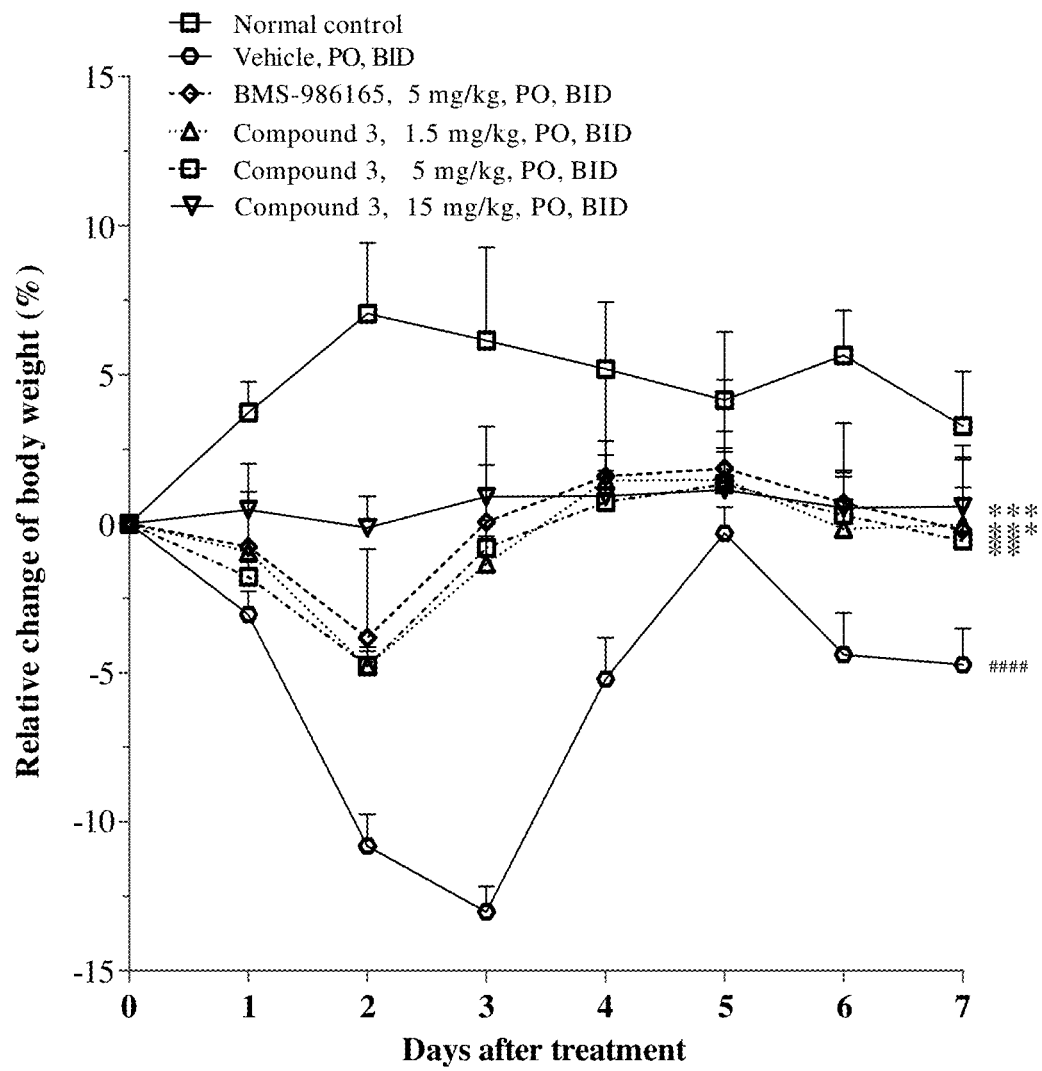
FIG. 2 shows in vivo efficacies in an anti-CD40 antibody induced IBD colitis animal model. Relative % changes of body weight of animals treated with vehicle, a reference compound, and Compound 3 at three different dosages are plotted against number of days after treatment.

Example 14. In Vivo Efficacy Evaluation in the Anti-$CD_{40}$ Antibody-Induced Colitis Animal Model The female CB17-Scid mice (8-10 weeks old, 18-20 g) from Beijing Vital River laboratory were randomly divided into 5 groups (n=8 per group). On Day 0, colitis was induced in mice each with a single intraperitoneal injection of 100 µg of FGK4.5 anti-CD40 mAb (BioXCell, Cat. No. EB0016-2) in PBS. Starting from Day 0 through 7, mice in the treatment groups were orally dosed with 0, 1.5, 5, 15 mg/kg of Compound 3 or 5 mg/kg of BMS-986165 in the vehicle of DMSO/solutol/PEG-400 (10:5:30) twice daily, while mice in the vehicle group were orally dosed with the above-mentioned vehicle. On a daily basis, mice were weighed and monitored for signs of colitis including body weight loss and the accompanying loose stools and diarrhea. On Day 8, all animals were euthanized. Spleen tissues were collected and weighed. The results show that Compound 3 at dosages 1.5 mg/kg, 5 mg/kg, and 15 mg/kg and the reference compound at 5 mg/kg significantly protected mice from colitis in preventing body weight loss (FIG. 2, Table 4) and spleen enlargement (Table 4) as comparing to mice in the vehicle group.

TABLE 4

| Group | | Relative change in body weight (%)* Day | | | | | | | | | Spleen weight (g) |
| --- | --- | --- | --- | --- | --- | --- | --- | --- | --- | --- | --- |
| | | 0 | 1 | 2 | 3 | 4 | 5 | 6 | 7 | 8 | 8 |
| Vehicle | Mean | 0.0 | −3.1 | −10.8 | −13.0 | −5.2 | −0.3 | −4.4 | −4.7 | −3.7 | 0.153 |
| | SEM | 0.0 | 0.8 | 1.1 | 0.9 | 1.4 | 0.9 | 1.4 | 1.2 | 1.1 | 0.011 |
| BMS-986165 5 mg/kg | Mean | 0.0 | −0.8 | −3.8 | 0.0 | 1.6 | 1.9 | 0.7 | −0.2 | −3.1 | 0.036 |
| | SEM | 0.0 | 2.8 | 3.0 | 3.2 | 3.3 | 3.0 | 2.7 | 2.8 | 1.9 | 0.003 |
| Cmpd 3 1.5 mg/kg | Mean | 0.0 | −0.9 | −4.8 | −1.3 | 1.5 | 1.5 | −0.2 | 0.0 | −3.7 | 0.060 |
| | SEM | 0.0 | 0.3 | 0.5 | 0.9 | 1.3 | 1.6 | 2.0 | 2.3 | 1.3 | 0.006 |
| Cmpd 3 5 mg/kg | Mean | 0.0 | −1.8 | −4.8 | −0.8 | 0.7 | 1.3 | 0.3 | −0.6 | −4.7 | 0.037 |
| | SEM | 0.0 | 0.5 | 0.6 | 0.9 | 1.1 | 1.2 | 1.3 | 1.8 | 2.2 | 0.002 |
| Cmpd 3 15 mg/kg | Mean | 0.0 | 0.5 | −0.1 | 0.9 | 0.9 | 1.1 | 0.5 | 0.6 | −1.4 | 0.025 |
| | SEM | 0.0 | 0.6 | 1.0 | 1.1 | 1.4 | 1.3 | 1.2 | 1.6 | 1.3 | 0.002 |

*The relative change in body weight (RCBW) is calculated according to the formula of RCBW (%) = (BWx − BW0)/BW0 × 100%, where BWx is the mean body weight on Day x and BW0 is the mean body weight on Day 0.
SEM: standard error of the mean.

It is to be understood that the foregoing describes preferred embodiments of the present invention and that modifications may be made therein without departing from the scope of the present invention as set forth in the claims.

What is claimed is:

1. A compound of Compound 3, or Compound 2, or Compound 1, or Compound 4, or a pharmaceutically acceptable salt thereof, Compound 3

Compound 2

Compound 1

Compound 4

2. The compound of claim 1, which is Compound 3, or a pharmaceutically acceptable salt thereof.

3. The compound of claim 1, which is Compound 2, or a pharmaceutically acceptable salt thereof.

4. The compound of claim 1, which is Compound 1, or a pharmaceutically acceptable salt thereof.

5. The compound of claim 1, which is Compound 4, or a pharmaceutically acceptable salt thereof.

6. A compound of Compound 6 or Compound 8, or a pharmaceutically acceptable salt thereof,

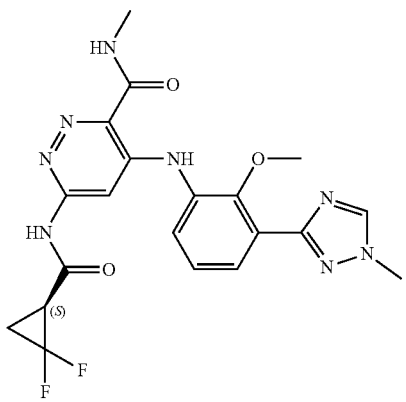

Compound 6

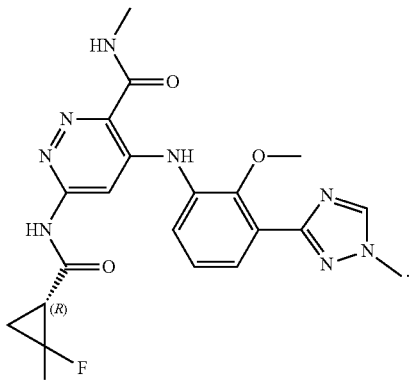

Compound 8

7. The compound of claim 6, which is Compound 6, or a pharmaceutically acceptable salt thereof.

8. The compound of claim 6, which is Compound 8, or a pharmaceutically acceptable salt thereof.

* * * * *